(12) United States Patent
Varalli et al.

(10) Patent No.: US 8,299,239 B2
(45) Date of Patent: Oct. 30, 2012

(54) PROCESS FOR THE PREPARATION OF GEMCITABINE HYDROCHLORIDE

(75) Inventors: Alberto Varalli, Gallarate (IT); Paolo Anesa, Milan (IT); Maria Argese, Sedriano (IT); Giuseppe Guazzi, Milan (IT)

(73) Assignee: Prime European Therapeucials S.p.A., Milan (IT)

( * ) Notice: Subject to any disclaimer, the term of this patent is extended or adjusted under 35 U.S.C. 154(b) by 422 days.

(21) Appl. No.: 12/582,955

(22) Filed: Oct. 21, 2009

(65) Prior Publication Data

US 2010/0105887 A1    Apr. 29, 2010

(30) Foreign Application Priority Data

Oct. 23, 2008  (IT) .............................. MI2008A1874

(51) Int. Cl.
C07H 19/073 (2006.01)
C07H 19/06 (2006.01)
C07H 1/06 (2006.01)

(52) U.S. Cl. ...................... 536/28.5; 536/127

(58) Field of Classification Search .................. None
See application file for complete search history.

(56) References Cited

U.S. PATENT DOCUMENTS

| | | | |
|---|---|---|---|
| 4,965,374 A | 10/1990 | Chou et al. | |
| 5,808,048 A * | 9/1998 | Berglund | 536/28.5 |
| 2004/0158059 A1 | 8/2004 | Tamerlani et al. | |
| 2008/0262215 A1 * | 10/2008 | Zelikovitch et al. | 536/28.5 |

FOREIGN PATENT DOCUMENTS

| | | |
|---|---|---|
| WO | 2005/095430 A1 | 10/2005 |
| WO | WO2005/095430 * | 10/2005 |
| WO | 2006/095359 A1 | 9/2006 |
| WO | 2007/049294 A1 | 5/2007 |
| WO | WO2007/112473 * | 10/2007 |

OTHER PUBLICATIONS

Wolfrom et al., "Sodium Borohydride as a Reducing Agent in the Sugar Series" Journal of the American Chemical Society (1952) vol. 74 pp. 5583-5584.*
Jiang et al., "An Improved Preparation Process for Gemcitabine" Organic Process Research and Development (2008) vol. 12 pp. 888-891.*
EP Search Report issued on Jan. 20, 2010 in counterpart EP 09 173 606.6.
Wang, et al., "Syhnthesis of Gemcitabine Hydrochloride," retrieved from STN Database Accession No. 2008:1103450 (Abstract), XP002542350.

* cited by examiner

*Primary Examiner* — Eric S Olson
(74) *Attorney, Agent, or Firm* — Lucas & Mercanti, LLP

(57) ABSTRACT

Disclosed is the preparation of 2-deoxy-D-erythro-2,2-difluoro-ribofuranose-3,5-dibenzoate,

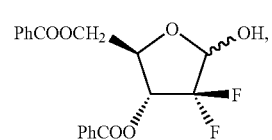

a known intermediate for the preparation of Gemcitabine, by means of a reduction process; further disclosed is the purification of Gemcitabine by chromatography and the purification of Gemcitabine hydrochloride by crystallization techniques from ternary solvent mixtures. The main advantage of the invention is providing Gemcitabine hydrochloride with purity in conformity with the Pharmacopoeia requirements, as well as a process particularly convenient from the industrial point of view.

4 Claims, No Drawings

PROCESS FOR THE PREPARATION OF GEMCITABINE HYDROCHLORIDE

This application claims priority to and the benefit of Italian Application No. MI2008A1874 filed on Oct. 23, 2008, the content of which is incorporated by reference in its entirety.

FIELD OF THE INVENTION

The present invention relates to Gemcitabine (2-deoxy-2',2'-difluorocytidine), a known antitumor drug, and intermediates and pharmaceutically acceptable salts thereof

BACKGROUND OF THE INVENTION

Gemcitabine (2-deoxy-2',2'-difluorocytidine)

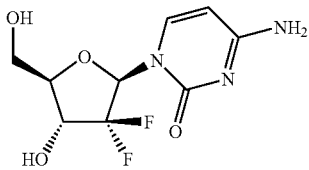

is disclosed in U.S. Pat. No. 4,526,988, which discloses a synthetic method comprising the preparation of 2-deoxy-D-erythro-2,2-difluoro-ribofuranose protected at the hydroxyls at the 3- and 5-positions with a suitable protective group P

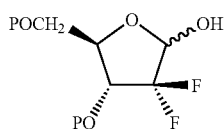

by reduction of 2-deoxy-D-erythro-2,2-difluoro-ribofuranos-1-ulose protected at the hydroxyls at the 3- and 5-positions

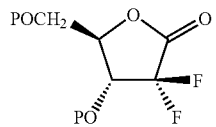

wherein P is as defined above
with a hydride, preferably with diisobutyl-aluminium hydride in toluene (DIBAL).

The reduction with lithium aluminium hydride was described in Chem. Abstr. XP 002542350. 2008:1103450.

U.S. Pat. No. 5,945,547 indicates benzoate as a particularly preferred protective group and it claims 2-deoxy-D-erythro-2,2-difluoro-ribofuranos-1-ulose-3,5-dibenzoate, while U.S. Pat. No. 4,965,374 claims a method for its recovery.

Protected 2-deoxy-D-erythro-2,2-difluoro-ribofuranose is subsequently transformed into Gemcitabine by transformation of the hydroxyl at the 1 position into a leaving group, preferably methanesulfonate, reaction with protected acetyl-cytosine to afford protected Gemcitabine and removal of the protective groups. Gemcitabine base can then be transformed into a pharmaceutically acceptable salt, such as the hydrochloride usually employed in therapy.

The synthesis of high purity Gemcitabine hydrochloride, according to the regulatory requirements contemplated by the Official Pharmacopoeias, requires purification of the beta anomer by separation of the alpha anomer, which is difficult and often involves costly chromatographies.

Moreover, the synthesis processes involving 2-deoxy-D-erythro-2,2-difluoro-ribofuranos-1-ulose-3,5-dibenzoate still suffer from some problems, such as the remarkable energy waste necessary to maintain the low temperatures (between −80 and −60° C.) required during the reduction reaction of the carbonyl group with DIBAL.

The known processes for the purification of Gemcitabine base from the hydrochloride involve the use of high volumes of solvent (70 to 100 volumes per gram of product) and are not ideal from the yield point of view. See in particular U.S. Pat. No. 4,965,374, WO 2006/095359, WO 2005/095430 and WO 2007/049294.

DISCLOSURE OF THE INVENTION

In a first aspect, the invention relates to a process for the preparation of 2-deoxy-D-erythro-2,2-difluoro-ribofuranose-3,5-dibenzoate:

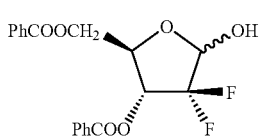

by reduction of 2-deoxy-D-erythro-2,2-difluoro-ribofuranos-1-ulose-3,5-dibenzoate

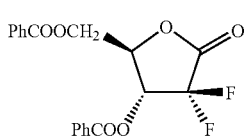

with calcium or sodium borohydride.

This reaction can be carried out with methods and reagents known to those skilled in the art; in particular aprotic polar solvents, e.g. tetrahydrofuran, ethyl acetate and dioxane, at a temperature ranging from −20 to +20° C., can be used; after completion of the reaction, 2-deoxy-D-erythro-2,2-difluoro-ribofuranose-3,5-dibenzoate can be transformed into Gemcitabine according to known methods, for example according to the process disclosed in U.S. Pat. No. 4,965,347, which comprises the transformation of the hydroxyl at the 1-position into a methanesulfonate group, the reaction with bis-trimethylsilyl-N-acetyl-cytosine in the presence of trimethylsilyl triflate and the removal of the protective groups. Examples 4-8 reported in the Experimental Section of the present application disclose in further detail the transformation of the intermediate into Gemcitabine according to the teaching of said Patent.

The preparation of 2-deoxy-D-erythro-2,2-difluoro-ribofuranose-3,5-dibenzoate by reduction of the precursor with calcium or sodium borohydride is particularly convenient from the industrial point of view in that it reduces the energy requirements of the process, as extremely low temperatures are no longer necessary.

In a second aspect, the invention relates to a process for the preparation of Gemcitabine hydrochloride in conformity with the pharmacopoeia requirements. The expression "in conformity with the pharmacopoeia requirements" means Gemcitabine hydrochloride having purity not lower than 99.8%, with Gemcitabine α anomer <0.1%, cytosine <0.1%, any other impurity <0.1%, total impurities <0.2% and titer ranging from 97.5% to 101.5. Said process comprises the purification of crude Gemcitabine (obtained according to known methods or using 2-deoxy-D-erythro-2,2-difluoro-ribofuranose-3,5-dibenzoate prepared as described above), on an ion exchange chromatographic column, the dissolution of the eluted Gemcitabine in methanol and the precipitation of the hydrochloride by addition of concentrated HCl (37%) and ethyl acetate. Chromatography is carried out with commercially available reagents and according to procedures known to those skilled in the art. The resin usually employed is a strong cation exchange resin; according to a particular embodiment, the resin is Amberlite IR 120. Typically, the resin is conditioned with water, after that a crude Gemcitabine aqueous solution is dissolved in water, loaded on the resin and eluted with an ammonia aqueous solution at increasing concentrations ranging from 5 to 20% by weight. The eluate is evaporated to dryness and the oil which is usually obtained, consisting of Gemcitabine base, is dissolved in methanol; then added with a 37% hydrochloric acid aqueous solution in stoichiometric amounts and an ethyl acetate volume approximately equivalent to the volume of the methanol solution; rapid formation of a precipitate, consisting of the hydrochloride, is observed. Usually, the mixture is left to stand overnight at a temperature of 5° C. to improve yields, before filtering and drying the product.

In a third aspect, the invention relates to a process for the preparation of high purity Gemcitabine hydrochloride starting from crude Gemcitabine (obtained according to known methods or using 2-deoxy-D-erythro-2,2-difluoro-ribofuranose-3,5-dibenzoate prepared as described above). This process comprises the dissolution of crude Gemcitabine in methanol and the subsequent addition of a concentrated hydrochloric acid aqueous solution and acetone or ethyl acetate; after addition of concentrated hydrochloric acid rapid formation of a precipitate is observed; then a volume of acetone or ethyl acetate equal to the methanol volume is added. Rapid formation of a precipitate, consisting of the hydrochloride, is observed. Usually, the mixture is left to stand overnight at a temperature of 5° C. before filtering and drying the product. Il volume of the crystallization solvent mixture is preferably of approx. 30 volumes per gram of product. The resulting hydrochloride usually as HPLC purity higher than 95% and lower than 98%.

In a fourth aspect, the invention relates to a process for the preparation of Gemcitabine hydrochloride in conformity to the Pharmacopoeia requirements, comprising the recrystallization of Gemcitabine hydrochloride from water, methanol and acetone or from water, methanol and ethyl acetate.

The volume of the crystallization solvent mixture is preferably of approx. 30 volumes per gram of product.

This process can be applied either starting from Gemcitabine hydrochloride with low HPLC titer, for example with titer below 85%, as illustrated in Example 12 of the present application, or starting from Gemcitabine hydrochloride with higher purity, obtained as described in the preceding paragraph. Comparison between the purity values and HPLC titer and content in the alpha form reported in Examples 11 and 12 and the values reported in Example 13 evidences that the use of water/methanol/acetone or water/methanol/ethyl acetate ternary mixtures for the recovery and recrystallization of Gemcitabine hydrochloride is remarkably advantageous over the use of a binary mixture consisting of water and acetone. The water/methanol/ethyl acetate mixture is particularly preferred.

In a fifth aspect, the invention relates to a process for the preparation of Gemcitabine hydrochloride comprising the following steps:

a) reduction of 2-deoxy-D-erythro-2,2-difluoro-ribofuranos-1-ulose-3,5-dibenzoate

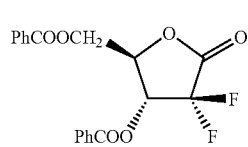

with calcium or sodium borohydride, to afford 2-deoxy-D-erythro-2,2-difluoro-ribofuranose-3,5-dibenzoate:

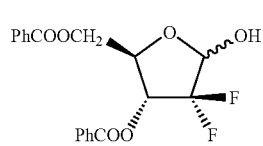

b) transformation of the hydroxyl at the 1-position into a leaving group and reaction with acetylcytosine to afford Gemcitabine base;

c) purification of Gemcitabine base by ion exchange chromatography;

d) dissolution of Gemcitabine base obtained at step c) in methanol and subsequent addition of a concentrated hydrochloric acid aqueous solution and acetone or ethyl acetate to afford a precipitate consisting of Gemcitabine hydrochloride;

e) recovery of Gemcitabine hydrochloride obtained at step d) and recrystallization from water, methanol and acetone or from water, methanol and ethyl acetate.

In step e) the use of a water, methanol and ethyl acetate mixture, in the ratios specified above, is preferred.

This process is particularly suitable from the industrial point of view in that it combines the advantages of the synthesis of the intermediate and those of the recovery and purification of the hydrochloride according to the invention.

The process of the invention is more advantageous than those disclosed in U.S. Pat. No. 4,965,374, WO 2006/095359, WO 2005/095430 and WO 2007/049294 from the standpoint of solvent volumes and tolerability thereof, which is markedly higher than that of monoglyme and dioxane described in WO 2007/049294 and of acetonitrile described in WO 2005/095430 and WO 2006/095359. Furthermore, the process of the invention has better efficiency and selectivity over the known processes as the recovery of the crude provides a product which is already 95-97% pure and which attains the desired quality through a single subsequent operation. Conversely, in WO 2005/095430 and WO 2006/095359 the crude has to be slurried in water before crystallization. U.S. Pat. No. 4,965,374 provides a product with satisfactory quality only after repeated, complex operations, as reported by way of comparison in the Examples.

The experimental section shows in detail the invention.

EXPERIMENTAL SECTION

Example 1

Preparation of 2-deoxy-D-erythro-2,2-difluoro-ribofuranose-3,5-dibenzoate with $Ca(BH_4)_2$ 0.19 g of $CaCl_2$ (1.99 mmoles) and 0.151 g of $NaBH_4$ (3.99 mmoles) were added to 4 ml of EtOH. The suspension was cooled to −20° C. and added with a solution of 2-deoxy-D-erythro-2,2-difluoro-pentafuranos-1-ulose-3,5-dibenzoate (5.0 g; 13.29 mmoles) in 20 ml of tetrahydrofuran during 45 minutes. After a further 60 minutes, the reaction was monitored by TLC (1:1 ethyl acetate:hexane) and after completion it was arrested by addition of 20 ml of ethyl acetate followed by concentrated HCl to pH=2. After stirring for 10 minutes at room temperature, the aqueous phase was separated and repeatedly extracted with ethyl acetate (20 ml), afterwards the combined organic phases were washed with brine (20 ml) and 5% $NaHCO_3$ aqueous solution (20 ml). The organic phase was concentrated under vacuum to give a thick oil (5.5 g). This product contained an impurity less polar than the product.

Example 2

Preparation of 2-deoxy-D-erythro-2,2-difluoro-ribofuranose-3,5-dibenzoate with $NaBH_4$ 100 g of 2-deoxy-D-erythro-2,2-difluoro-pentafuranos-1-ulose-3,5-dibenzoate (0.266 mole) was dissolved in a 2 L round-bottom flask in 650 ml of tetrahydrofuran and cooled to 2° C., after which 3.20 g of $NaBH_4$ (0.084 mole) was added. The suspension was stirred for 3 h, then a sample was taken and monitored by HPLC. After completion, the reaction was stopped by addition of 500 ml of brine and concentrated HCl to pH 2 (about 7 ml). The mixture was stirred for 10 minutes, then the aqueous phase was separated at room temperature; the organic phase was washed with 500 ml of brine, added with a further 500 ml of brine and the biphasic system was evaporated to remove THF; when an oil suspended in water was obtained, 500 ml of $CH_2Cl_2$ were added thereto. The mixture was stirred for 15 minutes, then the aqueous phase was separated and extracted again with 150 ml of $CH_2Cl_2$, then the combined organic phases were concentrated to give an oil (107 g). HPLC analysis showed purity of 75%; the calculated yield was 90%. Part of the oil was subjected to silica gel chromatography (eluent: 6:4 ethyl acetate-hexane) to give 3.0 g of pure lactol and 300 mg of impurity.

Example 3

Preparation of 2-deoxy-D-erythro-2,2-difluoro-ribofuranose-3,5-dibenzoate with $NaBH_4$ 10 g of 2-deoxy-D-erythro-2,2-difluoro-pentafuranos-1-ulose-3,5-dibenzoate (26.6 moles) was dissolved in a 250 ml round-bottom flask in 70 ml of AcOEt and cooled a 2° C., then added with 0.32 g of $NaBH_4$ (8.4 moles). The resulting suspension was stirred for two hours, then a sample was taken and monitored by HPLC. After completion, the reaction was stopped by addition of 70 ml of brine and concentrated HCl to pH 2 (about 7 ml). The mixture was stirred for 10 minutes, then the aqueous phase was separated at room temperature. The organic phase was washed with 70 ml of brine, then added with a further 70 ml of brine, separated from the aqueous phase and concentrated to give an oil (10 g). HPLC analysis showed purity of 75%. The calculated yield was 88%.

Example 4

Preparation of 2-deoxy-D-erythro-2,2-difluoro-ribofuranose-3,5-dibenzoate-1-methanesulfonate 101 g of 2-deoxy-D-erythro-2,2-difluoro-ribofuranose-3,5-dibenzoate in the form of an oil (0.227 moles calculated) was dissolved in a 2 L round-bottom flask in 600 ml of methylene chloride. This mixture was cooled at 0-+5° C. and kept under stirring, then added with 42.8 g of triethylamine (0.424 mole) and 37.4 g of methanesulfonyl chloride (0.327 mole) during 30 minutes. The reaction was stirred a 5° C. for 1 h, then a sample was taken and monitored by HPLC. After completion, the reaction was added with 250 ml of water and 7 ml of concentrated HCl to pH 2. The mixture was stirred for 10 minutes, then the phases were separated and the organic one was washed twice with 250 ml of brine (conc. 10%). The solution was concentrated to give an oil (115 g). HPLC analysis showed purity of 75%. The calculated yield was 80% on the lactone.

Example 5

Preparation of 2-deoxy-D-erythro-2,2-difluoro-ribofuranose-3,5-dibenzoate-1-methanesulfonate 5.60 g 2-deoxy-D-erythro-2,2-difluoro-ribofuranose-3,5-dibenzoate in the form of an oil obtained according to Example 3 (11.96 mmoles calculated) was dissolved in 250 ml a round-bottom flask in 60 ml of ethyl acetate. The mixture was cooled to 0-+5° C., added with 2.68 g of triethylamine (26.58 mmoles) and 1.52 g of methanesulfonyl chloride (13.29 moles) during 30 minutes. The reaction was stirred a 5° C. for 1 h, then a sample was monitored by means of TLC (toluene/MeOH 9:1). After completion, 50 ml of water and ml of AcOEt were added and the mixture was stirred for 10 minutes, then the phases were separated and the organic one was added with 2.6 ml of 18% HCl to pH 1. The mixture was stirred for 10 minutes, then the phases were separated and the organic one was washed with 50 ml of brine, then concentrated to give 6.2 g of a residual oil.

Example 6

Preparation of 2'-deoxy-2',2'-difluoro-N-1-acetyl cytidine-3',5'-dibenzoate

Following the process disclosed in U.S. Pat. No. 4,965,374 and using the following reagents: 88.7 g of acetyl cytosine (0.579 mole), 280 g of hexamethyldisilazane (1.735 moles), 4.4 g of ammonium sulfate (0.033 mole), 116 g of trimethylsilyl triflate (0.522 mole), 115 g of mesylate obtained according to Example 4 (0.202 mole calculated), 135 g of a thick oil were obtained, which contained 52.1 g of protected Gemcitabine (determined by HPLC).

Example 7

Preparation of 2'-deoxy-2',2'-difluoro-N-1-acetyl cytidine-3',5'-dibenzoate

Following the process disclosed in U.S. Pat. No. 4,965,374 and using the following reagents: 83.2 g of acetyl cytosine (0.543 mole), 333 g of hexamethyldisilazane (2.063 moles), 3.3 g of ammonium sulfate (0.025 mole), 132 g of trimethylsilyl triflate (0.594 mole), 115 g of mesylate (obtained according to Example 4) (0.202 mole calculated), 118 g of a thick oil were obtained.

Example 8

Preparation of Crude Gemcitabine Base

Following the procedure disclosed in U.S. Pat. No. 4,965,374, with 45.5 g of oil obtained according to Example 6, 15 g of a crude oil was obtained; HPLC analysis showed titer of 26.06% in the form β (3.78 g) and an α/β ratio=1.29.

Example 9

Purification of Gemcitabine on Ion Exchange Resin 80 ml of an aqueous solution containing 12.5 g of crude Gemcitabine free base was eluted over 230 ml of resin IR120 (capacity 1.9 meq/ml) and the resin was washed with 700 ml of water; the eluate contained impurities. Gemcitabine was eluted with 400 ml of 7.5% (w/w) ammonia solution in water, then elution was continued using 200 ml of a 13% ammonia solution and subsequently 100 ml of a 15% solution. The fractions containing the product were concentrated and dissolved in 60 ml of MeOH. This solution was added with 6 ml of conc. HCl and 70 ml of AcOEt and a precipitate quickly formed. The mixture was stirred for 1 h at room temperature and overnight at 5° C. The solid (Gemcitabine HCl) was filtered, washed with MeOH and dried under vacuum at 45° C. overnight (yield: 4.20 g; HPLC purity=98.8%; form α 3.3%; HPLC purity=96.35%.

Example 10

Preparation of Gemcitabine HCl

The oil obtained according to Example 8 (15 g) was added with 45 ml of MeOH and 3.7 g of 37% HCl at room temperature, after a few minutes a precipitate formed. After addition of 45 ml of AcOEt, the mixture was stirred for 2 h at room temperature, then overnight at 5° C. The solid was filtered and washed with 1 ml of cold MeOH and 2×2 ml of AcOEt to give 2.79 g of form β (HPLC purity: 97%; area corresponding to the content in form α: 2.7%).

Example 11

Preparation of Gemcitabine HCl 15 g of crude Gemcitabine free base obtained according to Example 8 was added with 45 ml of MeOH and 3.7 g of 37% HCl; after a few minutes a precipitate formed. After addition of 45 ml of acetone, the mixture was stirred for two hours 2 h at room temperature, then overnight at 5° C. The solid was filtered and washed with 1 ml of methanol MeOH and twice with 2 ml of acetone, to give 2.58 g of product enriched in the form β (HPLC purity 97%; area corresponding to the content in form α: 3%).

Example 12

Purification of Gemcitabine HCl from a Water-MeOH-AcOEt Ternary Mixture 3.5 g of Gemcitabine HCl (titer 83%; form β 95%, form α 5%) was dissolved in 10.5 ml of water and 30 ml of MeOH al 78-79° C.; the resulting clear solution was cooled to 70° C., then added with 42 ml of AcOEt. The mixture was cooled at room temperature and stirred for 2 h, then cooled at 5° C. for 1 h. The solid was filtered, washed with AcOEt and dried under vacuum at 45° C., to give 2.74 g of product (HPLC purity 99.9%; form α lower than 0.1%. HPLC titer=102.4%.).

Example 13

Purification of Gemcitabine HCl from a Water/Acetone Mixture (Reference Example According to U.S. Pat. No. 4,965,374)

3.5 g of Gemcitabine HCl (titer=83%; form β 95%, form α 5%) was dissolved in 14 ml of water at 90° C.; the clear solution was cooled to 50° C., then added with 350 ml of acetone. The mixture was cooled at room temperature, stirred for 2 h, cooled at 5° C. overnight and the product was filtered and dried at 45° C. overnight (yield: 3.14 g; HPLC purity=99.27%; form α=0.54%. HPLC titer=96.20%).

The invention claimed is:

1. Process for the preparation of Gemcitabine hydrochloride

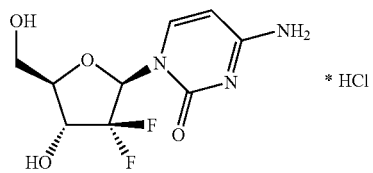

which comprises the purification of crude Gemcitabine by ion exchange chromatography, the dissolution of the obtained Gemcitabine in methanol and the precipitation of Gemcitabine hydrochloride from concentrated hydrochloric acid and ethyl acetate.

2. The process as claimed in claim 1 wherein the resin is a strong cation exchange resin.

3. The process as claimed in claim 2 which is carried out using a stoichiometric amount of concentrated hydrochloric acid and the same volume of ethyl acetate as the methanol volume necessary for dissolving the Gemcitabine obtained from the elution.

4. Process for the preparation of Gemcitabine hydrochloride comprising the following steps:

a) the reduction of 2-deoxy-D-erythro-2,2-difluoro-ribofuranos-1-ulose-3,5-dibenzoate

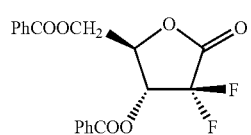

with calcium or sodium borohydride to afford 2-deoxy-D-erythro-2,2-difluoro-ribofuranose-3,5-dibenzoate:

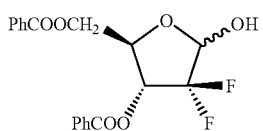 2a b) the transformation of the hydroxyl group at the 1-position into a leaving group and the reaction with acetylcytosine to give Gemcitabine base;

c) the purification of Gemcitabine base by ion exchange chromatography;

d) the dissolution of Gemcitabine base obtained at step c) in methanol and the subsequent addition of an aqueous solution of concentrated hydrochloric acid and ethyl acetate to give a precipitate consisting of Gemcitabine hydrochloride;

e) the recovery of Gemcitabine hydrochloride obtained at step d) and the recrystallization from water, methanol and ethyl acetate.

\* \* \* \* \*